(12) United States Patent
Brown

(10) Patent No.: US 10,695,210 B1
(45) Date of Patent: Jun. 30, 2020

(54) TELESCOPING COLLAPSIBLE SPLINT

(71) Applicant: Benjamin E. Brown, Charlotte, TN (US)

(72) Inventor: Benjamin E. Brown, Charlotte, TN (US)

(*) Notice: Subject to any disclaimer, the term of this patent is extended or adjusted under 35 U.S.C. 154(b) by 589 days.

(21) Appl. No.: 15/154,271

(22) Filed: May 13, 2016

Related U.S. Application Data

(60) Provisional application No. 62/162,375, filed on May 15, 2015.

(51) Int. Cl.
*A61F 5/058* (2006.01)
*A61F 5/30* (2006.01)

(52) U.S. Cl.
CPC ............ *A61F 5/05841* (2013.01); *A61F 5/30* (2013.01)

(58) Field of Classification Search
CPC ..... A61D 9/00; A61F 5/05841; A61F 5/0585; A61F 5/05858; A61F 5/05866; A61F 5/058; A61F 5/0111; A61F 5/0104; A61F 5/0106; A61F 5/0109; A61F 5/0113; A61F 5/0118; A63B 9/0057; A63B 9/0059; A63B 2069/0062
USPC ............................... 119/816, 820; 602/1–29
See application file for complete search history.

(56) References Cited

U.S. PATENT DOCUMENTS

| | | | | |
|---|---|---|---|---|
| 4,727,863 A | * | 3/1988 | Nelson ................ | A61F 5/0111 602/27 |
| 2003/0073942 A1 | * | 4/2003 | Gibbs .................. | A61F 5/028 602/19 |
| 2008/0251087 A1 | * | 10/2008 | Richardson .......... | A61F 5/0193 128/876 |

OTHER PUBLICATIONS

Merriam-Webster, definition of "enclose" (Year: 2019).*

* cited by examiner

*Primary Examiner* — Kari K Rodriquez
(74) *Attorney, Agent, or Firm* — Patterson Intellectual Property Law, P.C.; William E. Sekyi

(57) ABSTRACT

A collapsible splint includes an expandable frame within a flexible generally rectangular sleeve. The expandable frame includes a number of members that are extendable rods or tubes. The members are oriented longitudinally within the sleeve and arranged transversely across the sleeve and adjacent to one another. The rods are secured at one end of the sleeve and are connected to one another by transverse links to form the frame. The sleeve includes an opening through which the frame can be accessed and extended to a desired length. The sleeve also includes straps on its rear side suitable for binding the collapsible splint around a fractured limb.

13 Claims, 4 Drawing Sheets

TELESCOPING COLLAPSIBLE SPLINT

CROSS-REFERENCES TO RELATED APPLICATIONS

This application claims benefit of the following patent application(s) which is hereby incorporated by reference: U.S. Patent Application Ser. No. 62/162,375 filed on May 15, 2015.

BACKGROUND OF THE INVENTION

The present invention relates generally to a medical splint and immobilization device, more particularly to a lightweight, compact, telescoping splint.

Medical professionals, such as combat medics, emergency medics and paramedics at times need to attend to patients in remote or dangerous locations in combat, following natural or manmade disasters, or when performing other rescue operations. The difficult and remote circumstances under which these medical professionals must deliver medical attention frequently means that medics need to carry a large amount of heavy equipment on their person, or compactly packed in small, lightweight vehicles in which space and weight are at a premium. Medical military personnel, for example, must at times wear heavy cumbersome body armor, full loads of ammunition, weapons, numerous pieces of miscellaneous field equipment, as well as a large medical aid bag. They therefore frequently attempt to minimize the weight and size of equipment they choose to carry with them.

One piece of medical equipment that military and emergency rescue medics can consider important to take with them is a medical splint for use in an emergency to restrain movement of a fractured limb or portions of a fractured limb such as an arm, wrist, elbow, leg, knee or ankle following an attack, or accident. Commonly available splints, however, are generally large, heavy and cumbersome, and awkward to carry and store. Most are not easily adjusted and cannot conveniently support a wide variety of limbs, meaning that medics must at times carry several splints of different size. At other times, medics improvise using locally available materials that may not provide full support for the limb or may have unsuitable surfaces (e.g., sharp edges, splinters or an abrasive surface) that in the medic would not use as a splint in ideal circumstances. Additionally, to save weight and space, some splints can be too small and flimsy, providing insufficient support and permitting a braced limb to flex or twist under light impact that sometimes inadvertently occurs as a patient is being transported for additional medical care.

Thus, a need exists for an adjustable splint that is lightweight, that can be packed to a small size and that is easy to carry. Furthermore, a need also exists for a splint that is expandable to accommodate placement around an arm or leg but must also be strong enough to restrain and support a limb until the patient can receive attention in a medical facility.

BRIEF SUMMARY OF THE INVENTION

In one embodiment, a collapsible splint includes a sleeve having a pair of longitudinal edges and a pair of transverse edges that extend transversely between the longitudinal edges. The sleeve includes a plurality of straps configured to secure the sleeve around a human limb. The sleeve also includes a longitudinally expandable frame disposed within the sleeve. The frame has a plurality of longitudinally oriented and transversely arranged members, each member having a first member end secured adjacently to one sleeve end. Each member also has a second member end that is extendable from a first length to a second length adjacent the other sleeve end. Further, each member can be coupled by a plurality of transverse links to each adjacent member.

Optionally, the straps of the collapsible splint can include a plurality of first strap ends extending transversely from a first of the pair of longitudinal edges and a plurality of second strap ends extending transversely from a second of the pair of longitudinal edges. Each of the first strap ends can releasably couple with one of the second strap ends and the straps can be mounted on an exterior portion of the sleeve to slide longitudinally between the pair of transverse edges.

According to other alternative embodiments, the plurality of transverse links in the frame of the collapsible splint can include a flexible connector joined between adjacent rods. Also, the sleeve can have an opening, and in some embodiments, the opening can be at the other sleeve end.

A further embodiment provides a method of bracing a fractured limb. The method includes providing a collapsible splint, wherein the collapsible splint includes, a longitudinally expandable frame. The frame has a plurality of longitudinally oriented and transversely arranged members, each member having a first member end secured adjacently to one sleeve end and each member having a plurality of transverse links to each adjacent member. Each member also has a second member end defining a member length between the first member end and the second member end, and each member is extendable from a first length to a second length. The method also includes expanding the frame to a desired length, and binding the expanded frame to a limb.

In this method, binding the expanded frame to a limb can further include placing a limb longitudinally on the frame, encircling the limb with straps, transversely bending the frame around the limb, and tightening a plurality of the straps around the limb.

According to a further embodiment, the collapsible splint in this method can further include a sleeve enclosing the frame, the sleeve having a pair of longitudinal edges and a pair of transverse edges that extend transversely between the longitudinal edges. The sleeve can also have a plurality of straps configured to secure the sleeve around a human limb.

DETAILED DESCRIPTION OF THE INVENTION

Figure 1:
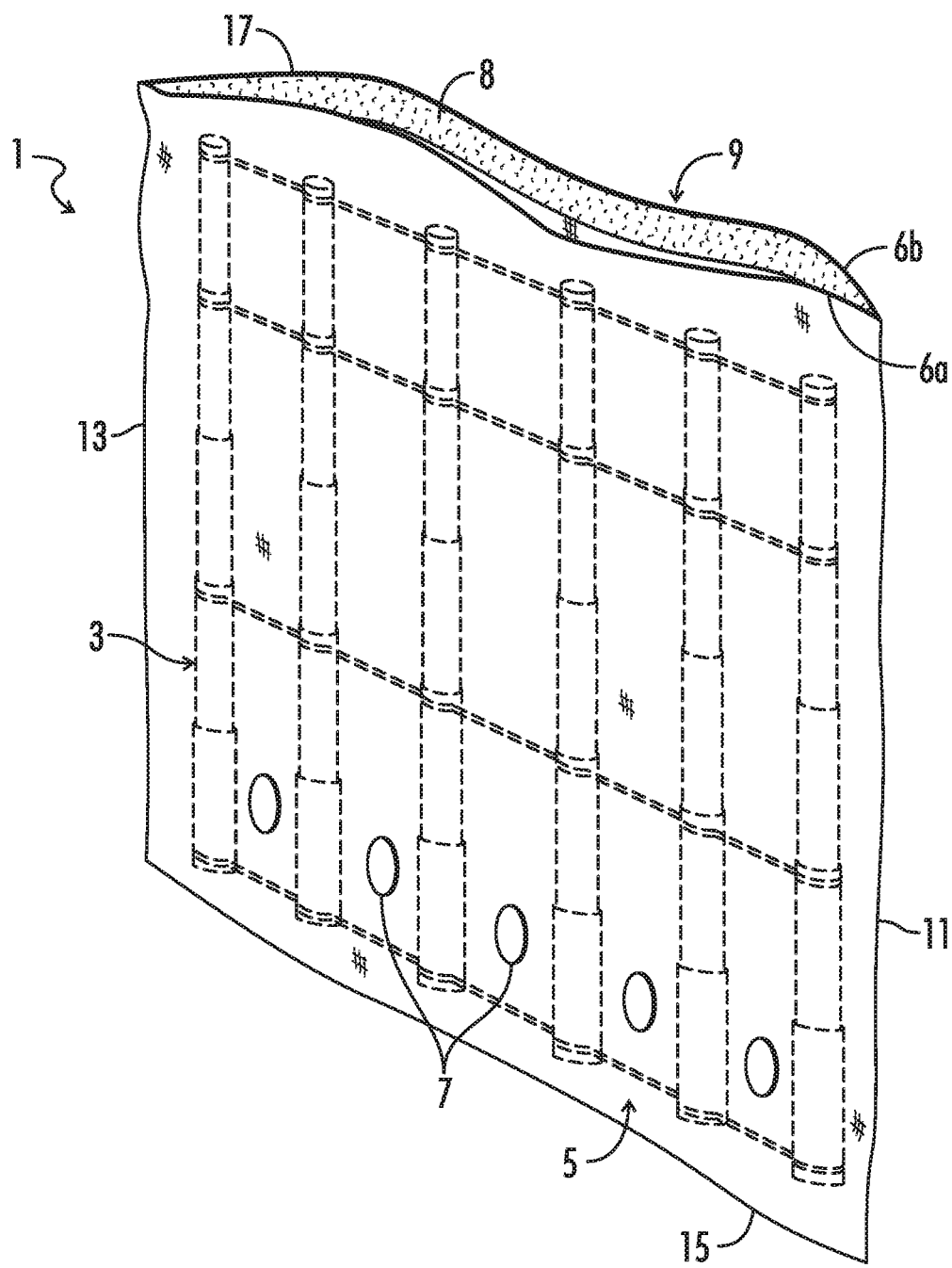
FIG. 1 is a front perspective view of a sleeve according to one embodiment of a collapsible splint including a frame shown in phantom lines.

According to one embodiment, the present invention provides an easily portable, telescoping, medical splint which is light in weight, withstands rigors of combat, and is easy to store and carry. Referring to FIG. 1, a collapsible splint 1 includes an expandable frame 3 within a flexible sleeve 5. Although sleeve 5 is not limited to a particular shape or size, in some embodiments, sleeve 5 can have a front side 6a and a back side 6b joined along a pair of longitudinal edges 11, 13 and a pair of transverse edges 17, 15 that extend transversely between longitudinal edges 11, 13. Thus, sleeve 5 can be generally rectangular in shape and, in some exemplary embodiments, can have longitudinal edges 11, 13 of about 34 inches in length and transverse edges 17, 15 of about 10 inches in length. Sleeve 5 can be made of a flexible woven or non woven web of material, such as a fabric, metallic, composite, plastic or other polymer material and can include an opening 9 to permit a user to access and manipulate frame 3.

One or both of sleeve sides 6a, 6b of sleeve 5 can also include padding to protect and cushion a braced fractured limb from the hard and potentially harsh surfaces of frame 3. It will be understood that several types of materials can be useful as padding material. The padding can include such materials as polyurethane foam rubber, open cell natural foam rubber, and extra high density urethane foam. Additional examples of suitable materials can include expanded, closed-cell or semi open cell foams containing polyvinyl chloride/nitrile-butadiene rubber, nitrile-butadiene rubber, neoprene, or ethylene-propylene-dienemethylene and blends of these materials. Extruded foams including styrene-butadiene rubber ethylene-propylene-dienemethylene, neoprene, nitrile-butadiene rubber and epichlorohydrin may also be suitable.

Expandable frame 3 can be made up of a number of members or rods 10 that are oriented or aligned to be generally parallel to the longitudinal edges 11, 13 of sleeve 5. Members 10 are sufficiently rigid to effectively brace a fractured limb. Individual members 10 are preferably spaced laterally between longitudinal edge 11 and longitudinal edge 13 in a transverse arrangement across sleeve 5. Members or rods 10 that make up the splint can be of any shape and size such as but not limited to, round, square, and hexagonal. The collapsed length and fully telescoped length is not limited to any size.

Figure 2:
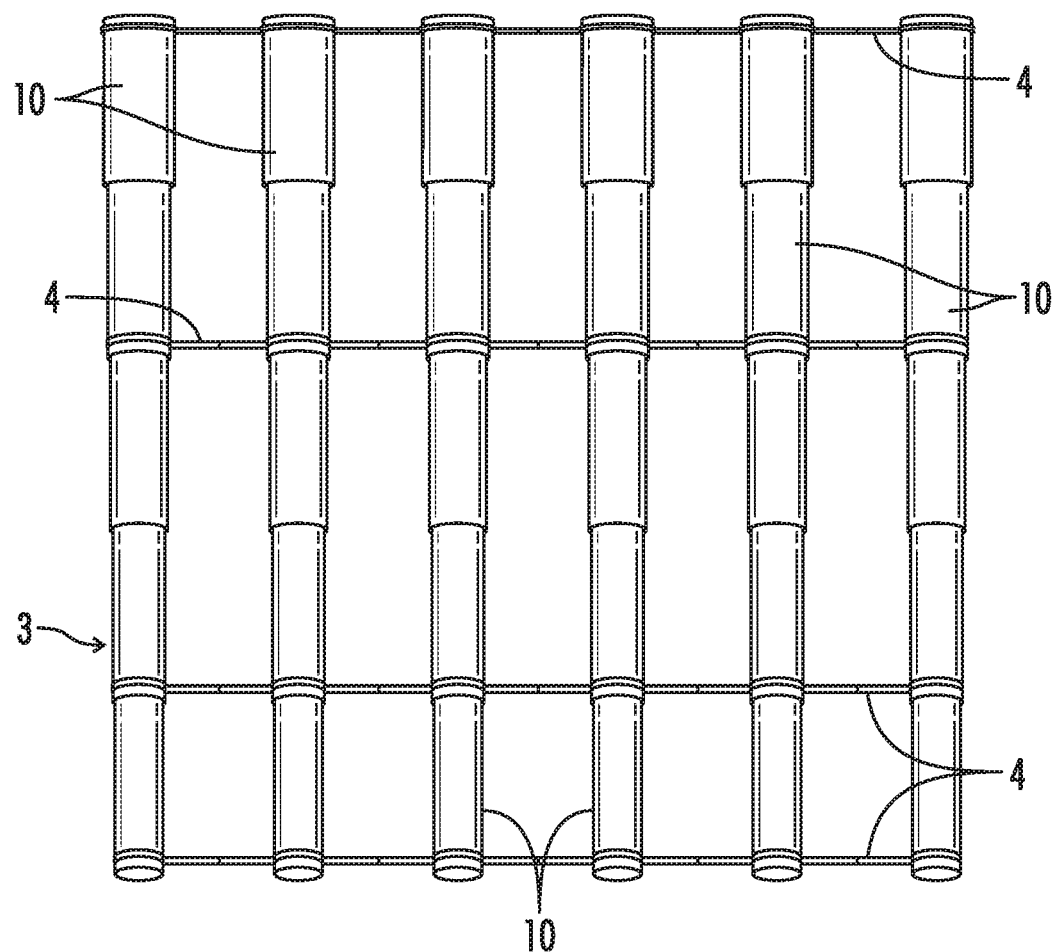
FIG. 2 is a front view of the frame of the collapsible splint in FIG. 1 with the frame expanded.

As shown in FIG. 2, transverse links 4 can connect adjacent members 10 to form frame 3. Links 4 preferably connect adjacent members 10 in a manner that provides sufficient flexibility to allow the frame 3 to bend laterally and conveniently conform around a fractured limb when deployed. Links 4 in combination with sleeve 3 should retain sufficient tensile strength to prevent frame members 10 from unduly separating, which could permit a braced limb to slip between members or otherwise bend, twist or distort about the limb fracture. Links 4 can be flexible connectors made of a variety of materials including but not limited to solid, stranded or braided metal wire, metal or plastic chain, or cording, such as parachute cord. Links 4 can also be flexurally rigid connectors made of rigid materials such as metal or plastic rods or tubes. These rigid connectors can be coupled to members 10 via hinged joints that permit frame 3 to bend and conform around a limb.

As shown in FIG. 1, first, proximate ends of members 10 are preferably arranged near or adjacent to a first transverse edge 15 of sleeve 5 with a row of transverse links 4 connecting members 10 near the first ends. Additional transverse links 4 can connect adjacent members 10 at locations spaced along the length of the members. For example, frame 3 preferably includes at least a second row of transverse links 4 connecting a second, distal end of members 10. Frame 3 can be secured in sleeve 5 near or adjacent the first transverse edge 15. It will be understood that various methods can be used to secure frame 3 in sleeve 5. For example, fasteners, such as rivets, screws, wires or stitching can penetrate sides 6a, 6b or edges of sleeve 5 and extend through into members 10, thereby securing members 10 to sleeve 5.

As a further example, fasteners 7 can extend through sides 6a, 6b of sleeve 5, at a distance longitudinally spaced from first transverse edge 15, and can thereby retain transverse links 4 at the first end of members 10 between the fasteners 7 and first transverse edge 15 of sleeve 5. Because these transverse links 4 are attached to members 10, they likewise hold the proximate end of members 10 and frame 3 near the first transverse edge 15. FIG. 4 shows an open sleeve 5 into which frame 3, as shown in FIGS. 2 and 3, can be fastened.

Members 10 can be made of any known material suitable for splints that are sufficiently rigid in flexure and sufficiently strong to brace a limb when formed into the shape of a member. As such, members 10 can be made of materials including, but not limited to, metal, wood, plastic, carbon fiber composite, and other composite materials.

Figure 3:
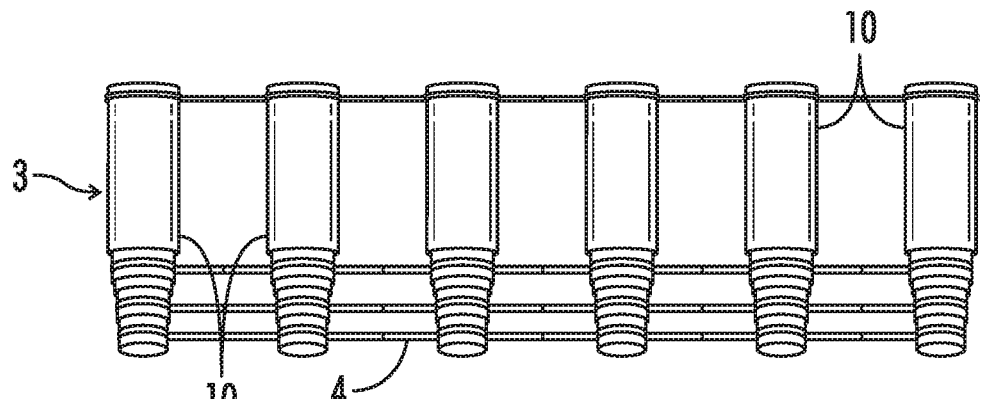
FIG. 3 is a front view of the frame of the collapsible splint in FIG. 1 with the frame collapsed.
Figure 4:
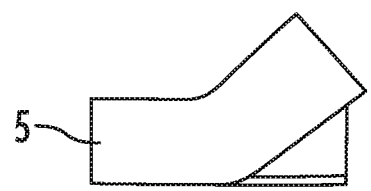
FIG. 4 is a side view of the collapsible splint sleeve partially closed.
Figure 5:
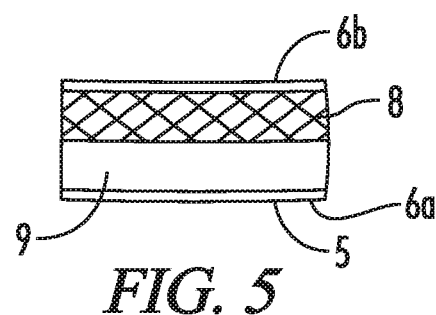
FIG. 5 is a side view of an opened end of the collapsible splint sleeve.

Members 10 are longitudinally expandable from a shortened collapsed length, as shown in FIG. 3, to a longer length that still retains flexural rigidity when extended, as shown in FIG. 2. When members 10 of frame 3 are collapsed, the excess length of sleeve 5 can be folded back onto the shorted members 10 and the folded collapsible splint 1 rolled into a compact spiral that is conveniently packed for storage and transportation. When fully lengthened the second, distal end of members 10 preferably extend to, or at least near, second transverse edge 17 of sleeve 5. Frame 3 preferably extends to a length sufficient to straddle a fracture in a broken limb and provide sufficient length on either side of the fracture to bind the limb to collapsible splint 1 using straps.

Because of the varying size of limbs and fractures, frame 3 is preferably also adjustable to intermediate lengths. Frame 3 can be expanded using several methods known in the art. In one example, each member 10 can comprise a number of telescoping rods or tubes. In such an arrangement, an assembly of rods or tubes is sequentially coupled with each other so that an outer diameter of a first rod or tube closely fits and slides along the inner diameter of a larger tube, and the outer diameter of the larger tube closely fits and slides along the inner diameter of a still larger tube. In this arrangement, a first or near end of one rod or tube can slide to a second or far end of another tube to lengthen and form an expanded rod assembly. The sequence of coupled rods or tubes can be repeated until the telescoping coupled rods or tubes achieve a desired total expanded length, as is known in the art.

According to an alternative embodiment, frame 3 can be expanded by adding additional rod or tube lengths to each member 10. Members can include male and female threads at opposing ends, for example, so that additional lengths of rods or tubes can simply be fastened to the end of each frame member 10. In yet another alternative, a number of rods or tubes can be hinged together end to end to fold on one another into a collapsed position, or to rotate through roughly 180 degrees into an open position and lock in a straight, extended position with respect to the adjacently hinged rod.

To deploy collapsible splint 1 and brace a fractured limb, a user can open sleeve 5 to access and lengthen frame 3 by reaching through opening 9, which can be located at any convenient position on sleeve 5. In one embodiment shown in FIG. 1, for example, opening 9 is located on second transverse edge 17 of sleeve 5. To prevent dirt and debris from entering sleeve 5 and corroding frame 3, rendering frame surfaces unhygienic, or causing the frame to jam when expanded or collapsed, opening 9 can include a resealing mechanism 8, such as hook and loop fabric, snap fasteners, or a zipper to close opening 9 as desired.

Figure 6:
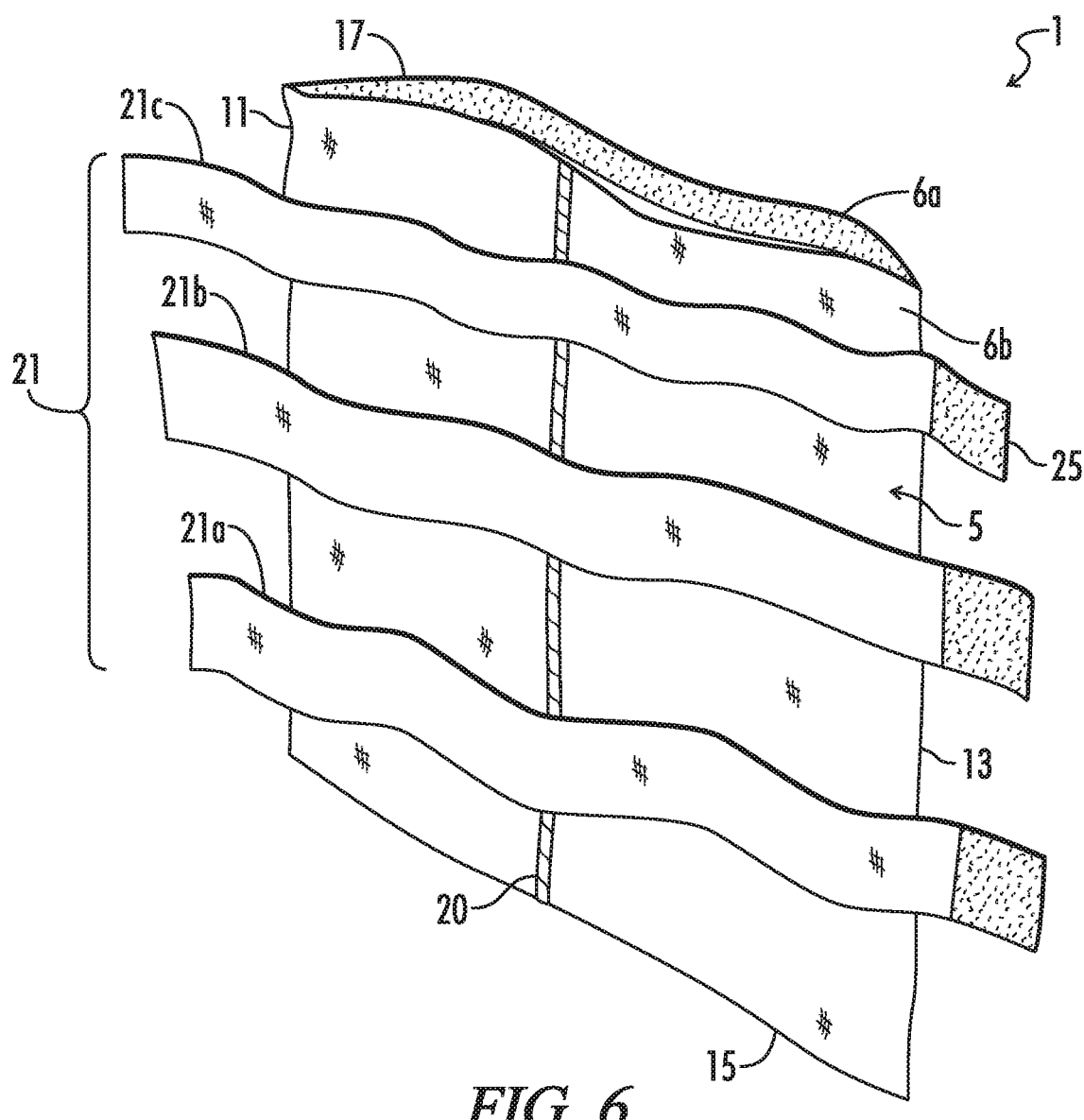
FIG. 6 is a rear perspective view of a sleeve according to an embodiment of the collapsible splint.

The rear side of collapsible splint 1 can include several straps 21a, 21b, and 21c, used to bind collapsible splint 1 to a limb. In the embodiment shown in FIG. 6, straps 21a, 21b and 21c can be mounted to slide along the length of sleeve 5 to adjust to varying lengths of frame 3 and to longitudinally reposition the straps 21 based on the different limbs that collapsible splint 1 may brace. It will be understood that straps 21 can be mounted to slide along the length of sleeve 5 using various known methods. For example, back side 6b of sleeve 5 can include cord 20 connected to run longitudinally generally at the middle of first transverse edge 15 and second transverse edge 17. Cord 20 can pass through loops at the middle of straps 21a, 21b, and 21c so that the straps are attached but can easily slide back and forth along cord 20, as shown in FIG. 6. Although FIG. 6 shows the collapsible splint 1 with three straps 21a, 21b, 21c, for illustrative purposes, it will be understood that that the collapsible splint 1 can have a larger or smaller number of straps 21.

Strap ends can include fastening mechanism 25 such as quick release buckles made of any material such as but not limited to metal or plastic, ties, clasps, clips or Velcro that allow one strap end to attach to another end. Thus, when a limb to be braced is placed on side 6a of the collapsible splint 1, the ends of straps 21 can be appropriately positioned and pulled around to encircle the limb and fastened together using fastening mechanisms 25. Preferably, fastening mechanisms permit strap ends to adjustably fasten to one another, so the straps can be progressively tightened around the limb to securely immobilize and brace the limb as necessary without causing undue pain, discomfort or dangerously inhibiting blood circulation in the limb.

According to one method, to use the collapsible splint 1 a user can pull and extend frame 3 by accessing frame 3 through opening 9 in sleeve 5. Once the frame 3 is extended to a desired length, user places collapsible splint 1 longitudinally under the limb in contact with front side 6a. User then encircles the limb with straps 21 on either side of the estimated location of the fracture and binds the limb to the collapsible splint 1 by tightening straps 21. As straps 21 tighten around a limb, they also draw in longitudinal edges 11 and 13 around the limb so that collapsible splint at least partially wraps around the limb. By at least partially wrapping around the limb, frame 3 of collapsible splint helps to immobilize the limb and stabilize the fracture, minimizing both lateral and transverse bending of the limb.

Thus, although there have been described particular embodiments of the present invention of a new and useful collapsible splint it is not intended that such references be construed as limitations upon the scope of this invention except as set forth in the following claims.

What is claimed is:

1. A collapsible splint comprising:
   a sleeve having a pair of longitudinal edges and a pair of transverse edges that extend transversely between the longitudinal edges, the sleeve having at least one strap configured to secure the sleeve around a human limb;
   a longitudinally expandable frame which, irrespective of the frame's expansion state, is capable of being entirely enclosed within the sleeve, the frame comprising a plurality of longitudinally oriented and transversely arranged members, each member having a first member end secured proximate to one sleeve end and a second member end that is extendable from a first length to a second length adjacent the other sleeve end, wherein each member is coupled by a plurality of transverse links to each adjacent member.

2. The collapsible splint of claim 1, further comprising a plurality of straps configured to secure the sleeve to a human limb, wherein the straps include a plurality of first strap ends extending transversely from a first of the pair of longitudinal edges and a plurality of second strap ends extending transversely from a second of the pair of longitudinal edges, wherein each of the first strap ends can releasably couple with one of the second strap ends.

3. The collapsible splint of claim 2, wherein the straps are mounted on an exterior portion of the sleeve to slide longitudinally between the pair of transverse edges.

4. The collapsible splint of claim 1, wherein the transverse links are flexible connectors coupled between adjacent members.

5. The collapsible splint of claim 1, wherein the sleeve includes an opening.

6. The collapsible splint of claim 5, wherein the opening is at the other sleeve end.

7. The collapsible splint of claim 1, wherein the sleeve includes a first side and a second side and wherein at least one side includes a padding layer.

8. A method of bracing a fractured limb comprising the steps of:
   providing a collapsible splint, wherein the collapsible splint includes,
   a longitudinally expandable frame which, irrespective of the frame's expansion state, is capable of being entirely enclosed within a sleeve of the collapsible splint, the frame comprising a plurality of longitudinally oriented and transversely arranged members, each member having a first member end secured adjacently to one sleeve end and each member having a plurality of transverse links to each adjacent member, wherein each member also has a second member end defining a member length between the first member end and the second member end, each member being extendable from a first length to a second length,
   expanding the frame to a desired length, and
   binding the expanded frame to a limb.

9. The method of claim 8, wherein binding the expanded frame to a limb further comprises,
   placing a limb longitudinally on the frame,
   encircling the limb with straps,
   transversely bending the frame around the limb, and
   tightening a plurality of the straps around the limb.

10. The method of claim 8, wherein the sleeve of the collapsible splint further includes
    a pair of longitudinal edges and a pair of transverse edges that extend transversely between the longitudinal edges, the sleeve also having a plurality of straps configured to secure the sleeve around a human limb.

11. The method of claim 10 wherein the sleeve includes an opening, and wherein expanding the frame to a desired length further includes accessing the frame through the opening to lengthen the frame.

12. The method of claim 11 wherein the straps are mounted on an exterior portion of the sleeve to slide longitudinally between the pair of transverse edges.

13. The method of claim 12, wherein binding the expanded frame to a limb further comprises,
    placing a limb longitudinally on the frame,
    adjusting the longitudinal placement of the straps and encircling the limb with the straps, transversely bending the frame around the limb, and tightening a plurality of the straps around the limb.

* * * * *